(12) United States Patent
Huang et al.

(10) Patent No.: US 7,588,904 B2
(45) Date of Patent: Sep. 15, 2009

(54) PERINUCLEOLAR COMPARTMENT AS A CANCER MARKER

(75) Inventors: Sui Huang, Chicago, IL (US); Rajesh V. Kamath, Chicago, IL (US); David Spector, Cold Spring Harbor, NY (US); Ann Thor, Winnetka, IL (US); Chen Wang, Chicago, IL (US)

(73) Assignees: Northwestern University, Evanston, IL (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 11/651,733

(22) Filed: Jan. 10, 2007

(65) Prior Publication Data

US 2007/0117168 A1 May 24, 2007

Related U.S. Application Data

(62) Division of application No. 10/403,422, filed on Mar. 31, 2003, now abandoned.

(60) Provisional application No. 60/368,822, filed on Mar. 29, 2002.

(51) Int. Cl.
*G01N 33/574* (2006.01)
(52) U.S. Cl. ..................... 435/7.23; 435/7.1
(58) Field of Classification Search .............. None
See application file for complete search history.

(56) References Cited

OTHER PUBLICATIONS

Wikepedia discussion of breast cancer (http://en.wikipedia.org/wiki/Breast_cancer, as downloaded on Apr. 27, 2007).*
Tockman et al (1992, Cancer Res. 52 (suppl.):2711s-2718s).*
Huang et al. (1997, J. of Cell Biology 137(5):965-974).*
Huttelmaier (2001, J. of Cell Biology 155(5):775-786).*
Medicinenet.com (www.medterms.com/script/main/art.asp?articlekey=5800 as downloaded Apr. 27, 2007).*
Bleyer et al, Cancer, 1978, 41:36-51.*
Huang et al., J. Cell Biol., 137:965 [1997].
Huang et al., J. Cell Biol., 143:35 [1998].
Ghetti et al., Nucl. Acids Res. 20:3671 [1992].
Patton et al., Genes & Dev. 7:393 [1993].
Gonzani et al., EMBO J.13:3356 [1994].
Singh et al., Science 268: 1173 [1995].
Ashiya and Grabowski, RNA 3:996 [1997].
Lin and Patton, RNA 1:234 [1995].
Perez et al., RNA 3:764 [1997].
Grossman et al., RNA 4:613 [1998].
Lou et aL, Genes Dev. 10:208 [1996].
Moreira et al, Genes & Dev. 12:2522 [1998].
Hellen et al., J. Virol. 68:941 [1994].
Kaminski et al., RNA 1:924[1995].
Witherell et al., Virology 214:660 [1995].
Kaminski and Jackson, RNA 4:626 [1998].
Montesano 1996, Intl J Cancer 69(3): 225-235.
Burmer 1991, Environmental Health Perspectives 93: 27-31.
Busken et al. 2003, Digestive Disease Week Abstracts and Intinerary Planner, abstract No. 850.
Tockman et al. 1992, Cancer Res. 52 (suppl.):2711s-2718s.
Huttelmaier 2001, J. of Cell Biology 155(5):775-786.

* cited by examiner

*Primary Examiner*—Misook Yu
*Assistant Examiner*—Mark Halvorson
(74) *Attorney, Agent, or Firm*—Casimir Jones, S.C.

(57) ABSTRACT

The present invention relates to compositions and methods for cancer diagnostics, prognostics and predictions, including but not limited to, cancer markers. In particular, the present invention provides perinucleolar compartments and their resident molecules as cancer markers.

7 Claims, 3 Drawing Sheets

PERINUCLEOLAR COMPARTMENT AS A CANCER MARKER

This application is a Divisional of U.S. application Ser. No. 10/403,422, filed Mar. 31, 2003, now abandoned which in turn claims priority to provisional patent application Ser. No. 60/368,822, filed Mar. 29, 2002; both of which are herein incorporated by reference.

This invention was made with government support under Howard Temin Award Training Grant No. K01 NCI; Grant No. 1 R01 CA77560-0181; and Grant No. 1 R21 CA84369-01 all awarded by the National Institutes of Health. The government has certain rights in the invention.

FIELD OF THE INVENTION

The present invention relates to compositions and methods for cancer diagnostics, prognostics and predictions, including but not limited to, cancer markers. In particular, the present invention provides perinucleolar compartments and their resident molecules as cancer markers.

BACKGROUND OF THE INVENTION

The development of cancer is a complex process involving the interplay of many genetic and epigenetic events. Cells undergo extensive biochemical and structural alterations throughout the course of cancer development. Tremendous efforts have been invested to increase the survival rate of cancer patients through the development of early detection programs and novel therapeutic strategies. Traditional histological standards for cancer diagnosis are well established and prognostic criteria routinely evaluated include size, invasiveness, involvement of adjacent structures or lymph nodes, metastases, and histological grade. More recently, advances in cellular and molecular techniques have fostered a better understanding of genetic and epigenetic changes during cancer development. An increasing number of molecular tumor markers have been identified to provide additional information for the diagnosis and prognosis of the disease. However, only a limited number of them have been reproducible and clinically relevant for cancer patient management. For most types of cancer, specific and sensitive markers that can predict the biological behavior of cancer cells (recurrence and metastases) are still lacking. What is needed are improved methods to specifically detect, characterize, and monitor the specific types and the progression of cancer. Furthermore, useful tumor markers that can accurately predict the outcome of patients suffering from cancers of various types and at various stages are desired.

SUMMARY OF THE INVENTION

The present invention relates to compositions and methods for cancer diagnostics, prognostics and predictions, including but not limited to, cancer markers. In particular, the present invention provides perinucleolar compartments and their resident molecules as cancer markers.

For example, in some embodiments, the present invention provides a method for predicting or prognosticating the recurrence or metastases of cancer comprising screening a sample from a subject (e.g., a human or other mammalian subject) for the presence of perinucleolar compartments; and determining if the subject is susceptible to recurrence or metastases of cancer based on the presence of perinucleolar compartments. In some embodiments, the screening step comprises identifying the prevalence of the perinucleolar compartments. In some preferred embodiments, the screening step comprises detecting polypyrimidine tract binding (PTB) protein. While the present invention is not limited by the method in which the perinucleolar compartments are detected, in some preferred embodiments, the screening step comprises immunostaining of said perinucleolar compartments.

In some embodiments, the method further comprises the step of selecting a therapy (e.g., chemotherapy) for the subject based on the presence of perinucleolar compartments. In some such embodiments, the prevalence of the perinucleolar compartments identifies the subject as being in a particular subset of subjects that is more likely to benefit from a particular therapeutic regimen. In some embodiments, the subject has previously been administered an anti-cancer therapy (e.g., chemotherapy).

The present invention also provides a method for predicting or prognosticating the recurrence or metastases of cancer comprising: screening a sample from a subject for the expression of PTB (e.g., protein or nucleic acid); and determining if the subject is susceptible to recurrence or metastases of cancer based on the amount of PTB expressed.

The present invention further provides methods for screening compounds (e.g., drugs), comprising: providing cancer cells (e.g., in vitro, ex vivo, in vivo) and a candidate drug; exposing the cancer cells to the candidate drug; and detecting the presence of perinucleolar compartments in the cancer cell. In some embodiments, a number of drugs are screened (e.g., using large compound libraries). In some embodiments, cells from multiple tissues are analyzed. In some preferred embodiments, the candidate drug comprises a candidate chemotherapeutic agent. In some embodiments, the method further comprises the step of selecting candidate drugs that affect the presence of perinucleolar compartments in the cancer cell.

The present invention also provides a kit (e.g., an in vitro diagnostic kit) comprising: a label that labels perinucleolar compartments (e.g., a molecule that finds use in direct or indirect detection of perinucleolar compartments); and a written component comprising instruction for performing a screen of a sample with the label such that a degree of malignancy of cells in the sample is determined (e.g., written instruction as mandated by the FDA regulations on in vitro diagnostic products). In some preferred embodiments, the label comprises an antibody (e.g., an antibody directed against PTB).

DEFINITIONS

Figure 1:
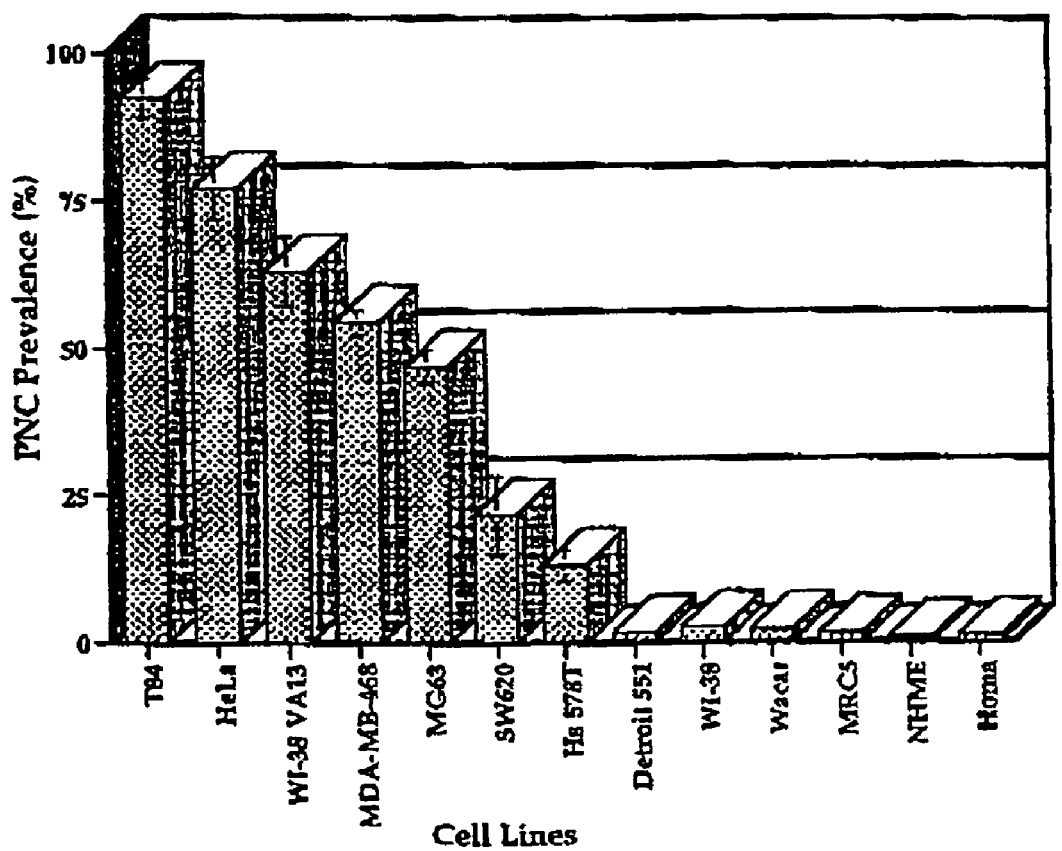
FIG. 1 provides a histogram showing that the percentage of cells that contain one or more PNCs (PNC prevalence) correlates with human cancer. The histogram indicates the statistical evaluation of PNC prevalence among human cancer cells and diploid cells.

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants." An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue and the stage of the cancer. Cancers may be characterized by the identification of the expression of or presence of one or more cancer markers, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient.

As used herein, the term "detecting a decreased or increased expression relative to non-cancerous control" refers to measuring the level of expression of a gene (e.g., the level of mRNA or protein) relative to the level in a non-cancerous control sample.

As used herein, the term "instructions for using said kit for characterizing cancer in a subject" includes instructions comprising the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. As used herein, the term "initial diagnosis" refers to results of initial cancer diagnosis (e.g. the presence or absence of cancerous cells).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein the term "portion" when in reference to a protein (as in "a portion of a given protein") refers to fragments of that protein. The fragments may range in size from four amino acid residues to the entire amino acid sequence minus one amino acid.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

GENERAL DESCRIPTION OF THE INVENTION

The present invention relates to compositions and methods for cancer diagnostics, including but not limited to, cancer markers. In particular, the present invention provides perinucleolar compartments as cancers markers.

The perinucleolar compartment (PNC) is an ribonucleoprotein (RNP) enriched subnuclear structure whose prevalence, as shown by experiments conducted during the development of the present invention, correlates with the degree of malignancy. In some embodiments of the present invention, the PNC is detected by an antibody (e.g., an monoclonal antibody) that specifically recognizes an RNA binding protein, polypyrimidine tract binding protein (PTB), highly enriched in the PNC. Any molecule associated with the PNC may be used and targeted to detect the PNC (e.g., antibodies directed against RNA binding proteins present in the PNC including, but not limited to, PTB, Raver1, nucleolin, Rpp40, CUG-BP, KSRP, and ROD1). Preferred RNA binding proteins for detection are those that stain strongly without strong labeling of other cellular components. Nucleic acid molecules (e.g., small RNAs transcribed in the PNC such as RnaseP, MRP RNAs, hY RNA, and SRP RNA) may also be used to identify the PNC. It is contemplated that PNC prevalence provides useful information regarding the degrees of malignant progression and chances of recurrences. As described below, the PNC is sensitive to a subset of anti-tumor drugs. Thus, the present invention also provides methods for monitoring therapeutic effects of particular chemotherapy drugs. Moreover, PTB changes its expression level and its nuclear distribution during malignant transformation. These alterations are indicative of the degree of cancer progression and also find use as markers for diagnosis and prognosis.

The perinucleolar compartment (PNC) is a dynamic, irregularly shaped, and electron dense nuclear structure that is physically associated with the nucleolus. The presence of the PNC is found predominantly in transformed cells in culture (Huang et al., J. Cell Biol., 137:965 [1997]) and in breast cancer tissue samples examined. Studies have shown that the PNC is involved in transcription and RNA metabolism (Huang et al., J. Cell Biol., 143:35 [1998]).

During the development of the present invention, a substantial amount of tissue samples from breast cancer at various stages were examined. It was found that PNC prevalence is statistically different among samples derived from cancers at various stages of malignancy. It is particularly interesting that PNC prevalence is significantly different between node negative breast cancer patients who later develop distal metastasis and node negative breast cancer patients who later do not develop distal metastasis. It was also found that PNCs disappear when cultured cells were treated with some of the routinely used chemotherapeutic drugs, particularly the ones involved in regulating transcription and RNA metabolism. Furthermore, quantitative Western blot analyses and immunohistochemical detection show that PTB, the heterogeneous nuclear RNP (hnRNP) protein marker for the PNC, is significantly elevated in malignant cells.

The present invention is not limited to the analysis of breast cancer. Experiments conducted during the course of development of the present invention further demonstrated that PNC prevalence is associated with colon cancer. Accordingly, in some embodiments, PNC prevalence is used to provide diagnostic, prognostic, and predictive information for colon cancers. The present invention contemplates the use of PNC prevalence for characterization of any type of cancer.

Thus, in some embodiments, the present invention provides compositions, kits, systems, and methods for detection of PNC and/or factor(s) expressed in PNCs as a means for detecting the presence of, or status of, one or more cancers. The present invention also provides screening methods for analyzing the effectiveness of compounds (e.g., drugs) at stimulating or inhibiting cell division, including an analysis of the effect of compounds on the management, treatment, or prevention of cancers. Since most patients treated with currently available chemotherapeutic agents suffer tremendously undesirable side effects, there is an urgent need to search for inhibitors of cancer expansion with minimal cytotoxicity. Accordingly, in some embodiments, the present invention provides methods of using the PNC as a marker to search for chemicals that eliminate the structure without killing the treated cells. In other embodiments, the present invention provides methods to search for chemicals that target cells with elevated PNCs (See e.g., Example 9).

PNC prevalence is indicative of the nature of the malignant cells and is used to predict the chance of recurrence in patients who are at the early stages of cancer development, thus providing guidelines for future therapeutic strategy. The finding of the PNC in benign lesions forecasts the possibility of these tumors becoming malignant. Experiments showed that the level of PTB correlates with the degree of malignancy and is used to evaluate the progression the disease. PTB can be detected using non-invasive protocols, when cancers originate in organs such as bladder, kidney, or uterus, by collecting bodily fluids.

PTB is a 57-kDa hnRNP protein that specifically binds pyrimidine rich RNA sequences (Ghetti et al., Nucl. Acids Res. 20:3671 [1992]). PTB has been shown to be involved in multiple cellular functions including pre-mRNA splicing (Patton et al., Genes & Dev. 7:393 [1993]; Gonzani et al., EMBO J. 13:3356 [1994]; Singh et al., Science 268:1173 [1995]; and Ashiya and Grabowski, RNA 3:996 [1997]), splice site selection in alternative pre-mRNA splicing (Lin and Patton, RNA 1:234 [1995]; Perez et al., RNA 3:764 [1997]; and Grossman et al., RNA 4:613 [1998]), RNA polyadenylation (Lou et al., Genes Dev. 10:208 [1996]; Moreira et al., Genes & Dev. 12:2522 [1998]), and translational regulation of certain viral RNA transcripts (Hellen et al., J. Virol. 68:941 [1994]; Kaminski et al., RNA 1:924[1995]; Witherell et al., Virology 214:660 [1995]; and Kaminski and Jackson, RNA 4:626 [1998]). PTB apparently participates in these functions through the binding of pyrimidine rich RNA sequences. Thus, PTB may serve as a bridge between the pyrimidine tract containing RNAs and a variety of cellular factors that fulfill different functions.

The advantages of detection of the PNC over existing tumor markers include, but are not limited to: 1) PNCs are easily identifiable, distinct structures; 2) PNC prevalence provides prognostic value for cancers that are detected at early stages; and 3) at least two distinct techniques can be used to detect and quantify resident molecules of the PNC.

The advantages of the present invention over existing methods are illustrated in the analysis of breast cancer. Breast cancer is a highly prevalent and morbid disease. Each year in the United States, about 110 new cases per 100,000 women are diagnosed, and 45,000 breast cancer patients die from the disease. Breast cancer is traditionally subclassified using the American Joint Committee on cancer staging guidelines (Lester and Cotran, Robbins Pathologic basis of disease, Cotran et al., eds., W.B. Saunders Company, 1093-1120, 1999). Stage I tumors are small and localized whereas stage IV patients have distant metastases. In general, survival rates decrease with disease progression. For lymph node positive patients, prediction of outcome is based predominantly on tumor size and histological grade. Approximately 10-20% of node-negative patients develop recurrence and distant metastases. Specific markers that can accurately forecast recurrence or metastases are not currently available. In addition to the classic histological criteria, a growing number of molecular genetic and immunocytochemical markers are being used or on trial to provide additional information for breast cancer diagnosis. For instance, 80-90% of breast cancer patients with hereditary link to family history have mutations in one of the two breast cancer genes BRCA1 and BRCA2 (See e.g., Duncan et al., J. Clin. Path. Clin. Mol. Path. Ed. 51:237 [1998]). The detection of mutations in BRCA1 and BRCA2 genes is now being used to monitor high-risk woman with genetic predisposition and prepare them for early diagnosis and effective treatment. In addition, estrogen and progesterone receptors have been shown to be associated with 50-85% of the breast cancers that are most commonly found in post-menopausal patients (See e.g., Ferguson et al., Cancer Treat. & Res. 94:255 [1998]). Another molecular marker erb-B2, a growth hormone receptor, is also found to be correlative with the aggressive behavior of breast cancer (See e.g., Mack et al., Human Path. 28:974 [1997]). While these markers provide important information in breast cancer diagnosis, and contribute to the prevention and treatment of the disease, they fall short in accurately predicting the future behavior of each breast cancer in forms of recurrence or metastases. Particularly for node negative patients, the methods of the present invention provide risk evaluation that is independent from other existing parameters of cancer prognosis. The present invention provides such a method, wherein the PNC represents collective changes of malignant transformation in cancer cells.

DETAILED DESCRIPTION OF THE INVENTION

Certain non-limiting, illustrative and preferred embodiments of the present invention are provided below.

PNC Detection

PNCs are detected using any suitable method. In some embodiments, PNCs are detected using immunohistolabeling methods using a monoclonal antibody specifically recognizing PTB (e.g., SH54; Huang et al., 1997, supra). In some embodiments, antigen retrieval-immunohistochemical technique is used to prepare paraffin-embedded tissue sections for optimal antibody-antigen interactions. The basic protocol involves deparaffinization and microwave retrieval for 2 minutes in 10 mM citric buffer pH 6.0, prior to conventional immunolabeling protocol (including incubation in primary antibody and subsequently in avidin conjugated secondary antibody). Immunolableing protocols are provided in Kamath et. al., 2002.

In some embodiments, flow cytometry is employed, as well as Enzyme-linked Immunosorbent Assay (ELISA) technique for quantification of the PTB protein. Hence, the present invention provides a marker that is detected by at least two different techniques, each technique being independent of the other.

1. Detection of RNA

In some preferred embodiments, detection of markers (e.g., PTB) is carried out by measuring the expression of corresponding mRNA in a tissue sample. mRNA expression may be measured by any suitable method, including but not limited to, those disclosed below.

In some embodiments, RNA is detection by Northern blot analysis. Northern blot analysis involves the separation of RNA and hybridization of a complementary labeled probe. In other embodiments, RNA (or corresponding cDNA) is detected by hybridization to a oligonucleotide probe. A variety of hybridization assays using a variety of technologies for hybridization and detection are available. For example, in some embodiments, the TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of cancer markers (e.g., PTB) is detected by measuring the expression of the corresponding protein or polypeptide. Protein expression may be detected by any suitable method. In some embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay is described in U.S. Pat. Nos. 5,599,677 and 5,672,480; each of which is herein incorporated by reference. The immunoassay described therein can be utilized to detect expression of resident molecules of the PNC 3. Kits In yet other embodiments, the present invention provides kits for the detection and characterization of cancer. In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

Antibodies

The present invention provides isolated antibodies. In preferred embodiments, the present invention provides monoclonal antibodies that specifically bind to an isolated polypeptide comprised of at least five amino acid residues of the cancer markers described herein. These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter with the antiserum and then measuring the activity of the labeling agent bound to the antibody. The cell fusion can be carried out according to known methods, for example, the method described by Koehler and Milstein (Nature 256:495 [1975]). As a fusion promoter, for example, Sendai virus (HVJ) or, preferably, polyethylene glycol (PEG), is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

EXPERIMENTAL

The following examples serve to illustrate certain preferred embodiments and aspects of the present invention and are not to be construed as limiting the scope thereof.

Example 1

The Presence of PNC is Correlated with the Transformed Phenotype

A large number of human cancer cell lines and normal human diploid cells were examined for the presence of PNC. The results showed that the PNC was predominantly present in cancer cells and was rarely found in normal, primary human cells. The result was evaluated statistically and summarized in the histogram in FIG. 1. PNC prevalence, the percentage of cells that contain a PNC, shows a large diversity among cancer cell lines examined. Some of the cell lines, such as HeLa (cervical epithelial carcinoma) and T84 (colon carcinoma) cells, show PNC prevalence of over 80%. In contrast, the PNC prevalence of other cell lines, including SW620 and MG63 cells, ranges from 25% to 50%. When a primary human diploid fibroblast, WI38, is transformed by SV40 large T antigen (WI38-VA13), the PNC prevalence rises to over 60% compared to 2% in its non-transformed parental cells.

Example 2

Evaluation of the PNC Prevalence in Breast Cancer Cells

To examine the presence of PNCs in breast cancer cells, a group of cancerous and normal breast cell lines were compared by PNC prevalence following immunolabeling with monoclonal antibody SH54. The results are shown in Table 1, below.

TABLE 1

|  | PNC prevalence % | Karyotype | Passage number | Tumor in nude mice |
|---|---|---|---|---|
| MDA-MB-157 | 41.8 +/− 3.2 | 52-69 | 39 | + |
| MDA-MB-468 | 52.3 +/− 4.6 | 60-67 | 332 | + |
| MDA-134-VI | 18.6 +/− 2.2 | 80-89 | 33 | − |
| MDA-MB-453 | 18.8 +/− 3.1 | 87-91 | 345 | − |
| Hs578T | 11.4 +/− 4.3 | 21-57 | Na | − |
| HNME | <1 | 46 | 18 | na |

Note:
MDA cells and H578T are clonal cell lines derived from breast adenocarcinoma or carcinoma.
HNME is human normal mammary epithelium.
na = not available.

This study demonstrates that there is no direct correlation between PNC prevalence and the number of chromosomes or the number of passages of cells in culture, showing that the formation of the PNC does not directly result from chromosome instability or tissue culture alterations. The data shows a positive correlation between PNC prevalence in the cell lines examined and the ability of these cells lines to be tumorogenic in nude mice.

Example 3

PNC Prevalence is Correlated with Degree of Malignancy

Figure 2:
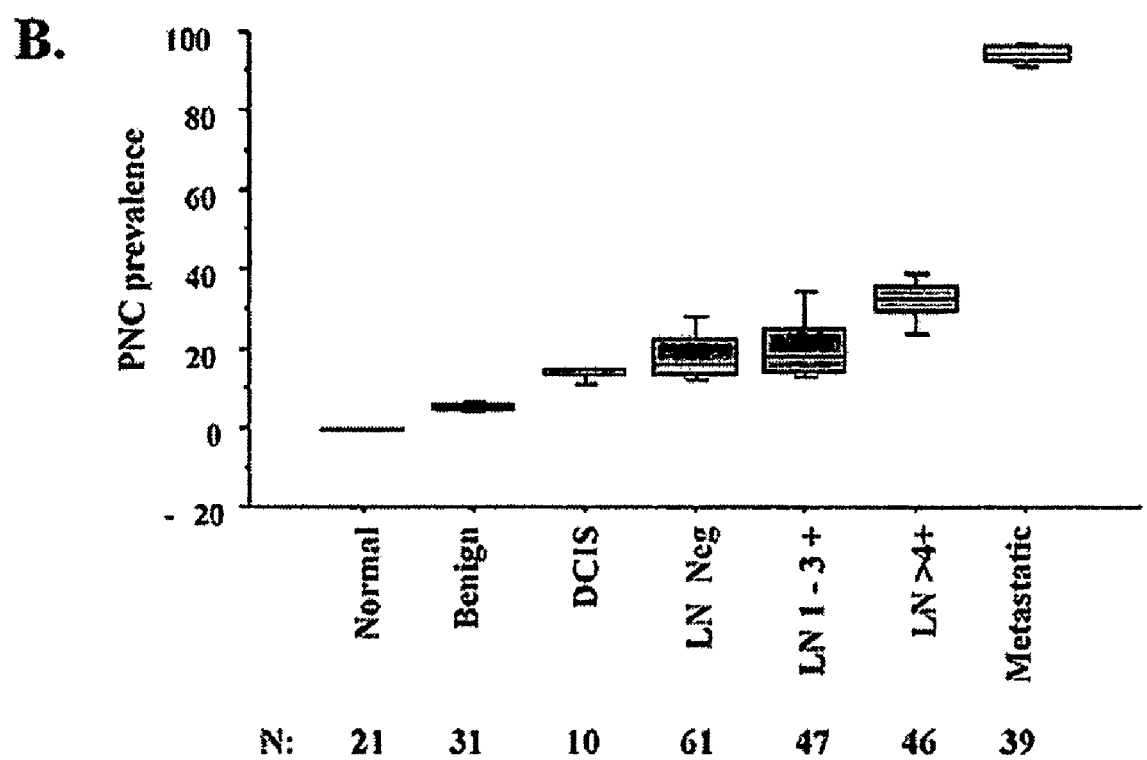
FIG. 2 shows quantitation of immunohistochemical staining of breast tissue samples at different stages of breast cancer progression.

Antigen retrieval-Immunohistochemical technique was performed on paraffin-embedded normal and cancerous breast tissue samples. SHH17, a monoclonal antibody that specifically recognizes PTB, was used to immunolabel the tissue samples. The immunostaining patterns of PTB show remarkable differences between normal and cancerous breast tissue samples. Five hundred or more cell nuclei were counted for PNC prevalence (defined as the percentage cells that contain one or more PNCs) in each tissue sample. The quantitative data are summarized in Table 2 and FIG. 2.

TABLE 2

| Comparison of PNC prevalence in normal and cancerous breast tissues | | | | | | | |
|---|---|---|---|---|---|---|---|
|  | Normal | Benign | In situ carcinoma | Invasive carcinoma | Invasive carcinoma | Invasive carcinoma | Invasive carcinoma | Metastic |
| Lymph node involved | − | − | − | − | − | Less than 4 | More than 4 |  |
| Recurrence as distal metastasis | − | − | − | − | + | + | + |  |
| Metastasis | − | − | − | − | − | − | − | + |
| No. of samples analyzed | 5 | 10 | 18 | 15 | 5 | 13 | 12 | 22 |
| Average percentage of cells positive for PNC marker per sample analyzed | 0 | 4.5% | 17.1% | 18.2% | 25.8% | 29.5% | 35.5% | 95% |

These experimental data show: 1) PNC prevalence correlates with the degree of malignancy; 2) In cancer patients with negative lymph nodes at primary diagnosis, there is a correlation between PNC prevalence and recurrence of the cancer. 3) The number of PNCs increases dramatically along with the progression of cancer from 1-2 per nucleus in carcinoma in situ to 10-20 per nucleus in metastatic cancers; 4) Multiple PNCs are present in nearly all cells of metastasized cancer.

Example 4

PTB Expression is Significantly Increased During Malignant Transformation

Quantitative Western blot analyses on various normal and cancerous cell lines in culture system demonstrated that PTB expresses at least ten fold higher in tumor cells lines than normal primary human fibroblasts. For example, in one experiment, cell lysates containing equal amounts of protein measured by a protein quantitation kit (BCA protein assay, Pierce) were loaded on the same gel (further confirmed by Ponceau S staining of the filter) and blotted with monoclonal antibody SH54, showing the 10-fold increase.

These observations are further supported by the immuno-labeling of various normal and cancerous breast tissues with SHH17. The level of PTB is similar between the nucleus and the cytoplasm in normal breast tissues. With the progression of the malignancy, PTB becomes highly enriched in the nucleus and forming multiple PNCs.

Example 5

PNCs Disappear Upon Treatment with Therapeutic Agents

Cultured HeLa cells, whose PNC prevalence is above 95%, were treated with various chemotherapeutic drugs. The observations are summarized in Table 3.

TABLE 3

| Drug | Category | Dose | Effect on PNC |
| --- | --- | --- | --- |
| Cisplatin | Pol I inhibitor | 0.5 µg/ml, 5 hours | 95% cell negative for PNC |
| Actinomycin D | Pol I inhibitor | 0.04 µg/ml, 2 hours | 100% cell negative for PNC |
| Campothecin | Anti-Topoisomerase I | 1.25 to 2.5 µg/ml, 1 hour | 100% cell negative for PNC |
| Methotrexate | RNA Anti-metabolite | 0.5 µg/ml, 16 hours | 30% cells negative for PNC |
|  |  | 1.0 µg/ml, 16 hours | 60% cells negative for PNC |
|  |  | 2.5 µg/ml, 16 hours | 80% cells negative for PNC |
| 5'-fluorouracil | RNA Anti-metabolite | 1 to 5 µg/ml, 16 hours | No effect on PNC structure |
| Paclitaxel | Anti-mitotic | 5 to 40 µM, 16 hours | No effect on PNC structure |
| Vincristine | Anti-mitotic | 5 to 40 µM, 16 hours | No effect on PNC structure |
| Hydroxyurea | DNA anti-metabolite | 0.5 to 1.5 µM, 16 hours | No effect on PNC structure |
| Cytosine Arabinoside | DNA anti-metabolite | 10 to 40 µg/ml, 16 hours | No effect on PNC structure |
| AMSA | Anti-Topoisomerase II | 5 to 40 µM, 16 hours | No effect on PNC structure |
| Adriamycin | Anti-Topoisomerase II | 5 to 40 µM, 16 hours | No effect on PNC structure |

These data demonstrate that PNC prevalence is reduced in cells treated with some chemotherapeutic agents. For methotrexate, the response is dose-dependent.

Example 6

PNC Prevalence Contains Independent Prognostic Information for Early Stage Breast Carcinoma Patients To analyze the relationship between PNC prevalence in primary tumors and the outcome of those patients, univariate analyses were performed. PNC prevalence, patient age, histological tumor grade, tumor size, ER status or PR status were each shown to be significantly associated with disease free survival (DFS) (Table 4A and B). However, only PNC prevalence, histological tumor grade, and tumor size were significantly associated with overall survival (OS) (Table 4A). A separate univariate analysis showed that PNC prevalence was inversely correlated with DFS in patients with negative nodal status p<0.0001), with 1-3 LN positive (p<0.0128) or with ≧4 LN positive (p<0.0304). These results suggest that PNC prevalence contains prognostic information.

TABLE 4

| A. Univariate Analysis for Factors associated with Survival | | | | | | | |
|---|---|---|---|---|---|---|---|
| | | DFS | | | OS | | |
| Factors | n | odd ratios | 95% CI | p-value | odd ratios | 95% CI | p-value |
| Age < 50 | 52 | 1 | | | 1 | | |
| Age ≧ 50 | 77 | 0.378 | (0.21, 0.67) | 0.0009 | 1.006 | (0.61, 1.65) | 0.98 |
| Size ≦ 2 cm | 56 | 1 | | | 1 | | |
| Size > 2 cm | 68 | 2.336 | (1.22, 4.48) | 0.0105 | 2.038 | (1.19, 3.48) | 0.0092 |
| LN neg | 59 | 1 | | | 1 | | |
| LN pos | 70 | 1.34 | (0.76, 2.36) | 0.31 | 1.237 | (0.76, 2.01) | 0.39 |
| LN = 0 | 59 | 1 | | | 1 | | |
| LN 1–3 | 26 | 1.462 | (0.70, 3.04) | 0.56 | 1.271 | (0.67, 2.41) | 0.69 |
| LN4+ | 44 | 1.272 | (0.67, 2.41) | | 1.217 | (0.70, 2.11) | |
| ER neg | 43 | 1 | | | 1 | | |
| ER pos | 78 | 0.46 | (0.26, 0.83) | 0.0094 | 0.637 | (0.38, 1.06) | 0.08 |
| PgR neg | 59 | 1 | | | 1 | | |
| PgR pos | 54 | 0.482 | (0.26, 0.88) | 0.0193 | 0.681 | (0.41, 1.15) | 0.15 |
| PNC < 18.6 | 46 | 1 | | | 1 | | |
| PNC ≧ 18.6 | 83 | 4.018 | (1.80, 8.97) | 0.0007 | 2.048 | (1.16, 3.61) | 0.013 |
| PNC < 23.6 | 64 | 1 | | | 1 | | |
| PNC ≧ 23.6 | 65 | 1.907 | (1.16, 3.14) | 0.0113 | 1.907 | (1.16, 3.14) | 0.0113 |
| Grade I | 42 | 1 | | | 1 | | |
| Grade II | 38 | 2.568 | (1.07, 6.15) | 0.0011 | 2.273 | (1.14, 4.53) | 0.0054 |
| Grade III | 45 | 3.944 | (1.78, 8.77) | | 2.855 | (1.50, 5.42) | |

| B. Cox Proportional Hazards Model Multivariate Survival for Lymph Node Negative Patients | | | | | |
|---|---|---|---|---|---|
| Factors | n (patients) | n events | chi square | Δ chi square[a] | p value |
| DFS | | | | | |
| Grade | 56 | 20 | 7.205 | | |
| Grade + PNC | 56 | 20 | 15.14 | 11.742 | 0.0048 |
| OS | | | | | |
| Size + Grade | 56 | 27 | 8.811 | | |
| Size + Grade + PNC | 56 | 27 | 13.614 | 4.803 | 0.0284 |

[a] Δ Chi square, change in the chi square from the base model using the log-rank statistic
n = number of patients;
age = patient age at the time of diagnosis;
ER status, negative (<10 fmol/mg protein or <20% immunopositivity) or positive (10 fmol/mg protein or 20% immunopositivity);
LN, lymph node.
All values are calculated as continuous variables except ER and PR, which were calculated as a negative or positive value.
PNC prevalence 18.6, median for all cases tested, and 23.6, median for all primary invasive cases with follow up.

Figure 3:
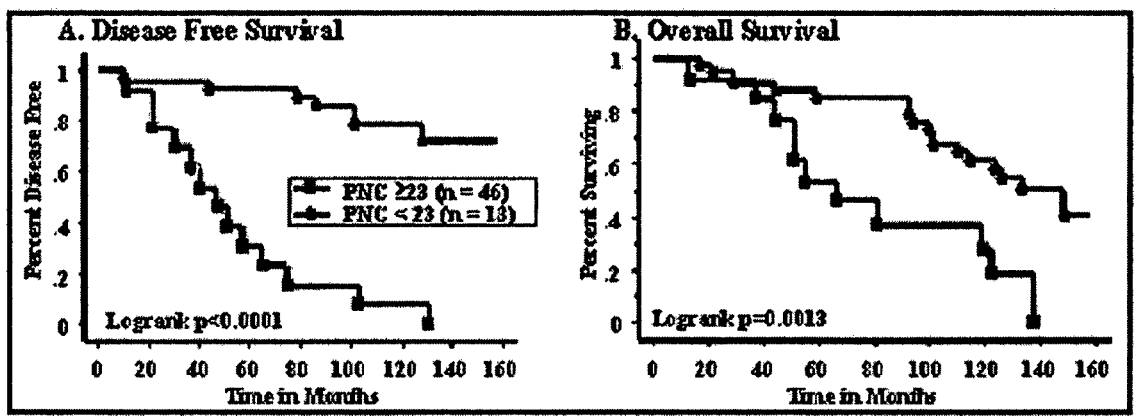
FIG. 3 shows Kaplan-Meier survival curves for breast cancer patients.
Figure 3:
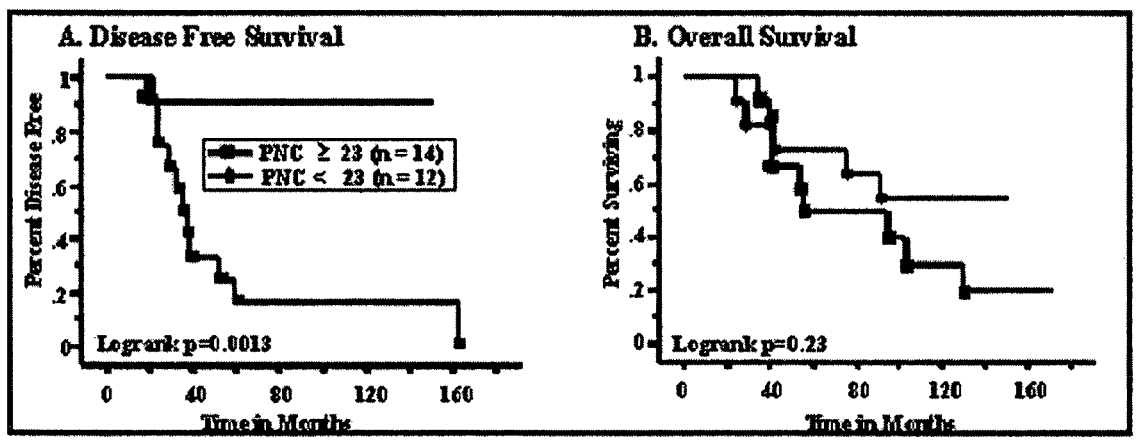

Further studies using multivariate analyses demonstrated that adding PNC prevalence to tumor grade and size significantly improve the survival prediction model for both DFS and OS in node negative patients (Table 4B). Kaplan-Meier analyses (See FIG. 3) graphically demonstrate these survival associations using the median PNC prevalence for invasive carcinoma (23%) as the cut off value. Patients with node negative or with less than 4 node positive tumors, but with high PNC prevalence ($\geq$23%) had a significantly shorter disease free survival, as compared to similarly diagnosed patients with low PNC prevalence (<23%) (p=0.0013). Altogether, the analyses indicate that PNC prevalence has independent prognostic value for early stage invasive carcinoma patients.

Example 7

Standardized Protocol for Scoring PNC Prevalence in Paraffin Embedded Sample Sections This Example describes a standard protocol to score PNC prevalence in paraffin embedded tissue samples. The PNC are detected by immunocytochemical labeling using an antigen retrieval protocol with monoclonal antibodies (SH54 or SHH17) that specifically recognize one of the PNC-associated proteins, PTB. The basic protocol involves deparaffinization and microwave antigen retrieval for 2-3 minutes in 10 mM citric buffer (pH 6.0), prior to the conventional immunolabeling protocol (including incubation with primary antibody and subsequently with avidin conjugated secondary antibody). Signals are detected using horseradish peroxidase (HRP) conjugated biotin that binds to avidin. The enzyme converts 3,3'-Diaminobenzidine (DAB) into dark precipitates (Spector, 1997 Cells: A Laboratory Manual. Cold Spring Harbor Laboratory Press. 2100 pp). Signals are visualized using light microscopy and images are captured through a 60× objective using a SenSys CCD camera (Princeton Instrument) that is controlled by the Metamorph image acquisition system (Universal Imaging). Nuclear PTB labeling aggregates that are at least 2-fold higher in intensity than the diffuse nucleoplasmic labeling are scored PNC-positive. The labeling intensity is determined using the densitometry software contained in the Metamorph image acquisition system. At least 500 epithelium cells in contiguous at the diseased area (the most aggressive areas, i.e., histologically high grade areas) are evaluated and scored for PNC prevalence. The scoring is performed in a blind manner such that examiners are unaware of the patient information (e.g., tumor size, nodal status, and patient outcome). Paraffin embedded HeLa cells, whose average PNC prevalence is 97%, are used as a positive control. Normal breast tissues (NCI shared tissue network) are used as a negative control for each round of labeling and scoring.

Tissue samples were generally fixed in buffered formalin from 2 hours to overnight. HeLa cells that were fixed either for 2 hours or overnight did not show significant difference in their PNC prevalence, demonstrating that the antigen-retrieval labeling method is not obviously affected by the length of fixation. Most samples were put in fixatives from less than one hour to several hours after the stop of blood supply. The ones that were not immediately fixed were temporally stored at 4° C. Samples with deteriorated cellular morphology were not selected for database or for studies.

In some embodiments, an automated scoring method is utilized to minimize the potential human errors. Threshold is used to distinguish the differences in labeling intensity. Each nucleus is evaluated individually due to slight differences in overall nuclear labeling intensity from cell to cell. However, the ratio of PNC labeling vs. the diffused nuclear labeling should remain similar.

Example 8

Drug Screening Assay

The following example provides an assay that finds use for identifying compounds that affect PNC prevalence.

The PNC as a marker can be detected easily by immunofluorescence using the specific monoclonal antibody, SH54, that recognizes PTB. The fluorescence intensity of PTB labeling is at least ten fold stronger in the PNC over the diffuse nuclear labeling. The step-wise screening protocol is following:

1) Cells with PNC prevalence over 95% are cultured in 96 well plates. Chemical libraries are added to the corresponding wells in concentrations initially at an µM range. Cells are cultivated in the presence of drugs for 1-2 days. The initial screening uses two different concentration and two different treatment durations and allows evaluation of 100 chemicals each day. A chemical library containing 800 chemicals can be screened within 2 weeks using these methods.

2) Cells are fixed in paraformaldehyde at 24 or 48 hours after drug additions, and are immunolabeled with SH54. The labeling signals are detected by incubation with a FITC conjugated secondary antibody. The cells are also counter stained with Dapi stain (a DNA specific dye to evaluate cell death).

3) Labeled cells are visualized in the 96 well plates on an inverted Zeiss Axiovert 135 fluorescence microscope and are scanned manually for surviving cells and the presence or absence of PNC in these cells.

The end point of the screening measures two parameters: a) cellular survival; and b) a reduction of PNC prevalence from 95% to below at least 50% or a reduction of the size of PNC to pin-points from normally irregular structures.

4) Once initial candidate chemicals are identified, more elaborate cellular characterizations is carried out including global status of chromatin structure, transcription, translation and cytoskeleton organization etc. Simultaneously, animal cancer models are used to test the effectiveness of the chemical in inhibition of tumor growth.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method of identifying the metastatic stage of breast cancer progression comprising:
   a) providing breast cancer tissue from a subject, wherein said breast cancer tissue comprises cells;
   b) identifying the prevalence of perinucleolar compartments in said breast cancer tissue at a level of about 95% to 100% of said cells comprising detecting perinucleolar compartments in said cells; and
   c) correlating said prevalence of perinucleolar compartments in said breast cancer tissue with the metastatic stage of breast cancer progression in said subject.

2. The method of claim 1, wherein said subject comprises a human subject.

3. The method of claim 1, wherein said identifying comprises detecting polypyrimidine tract binding (PTB) protein.

4. The method of claim 1, wherein said identifying step comprises immunostaining of said perinucleolar compartments.

5. The method of claim 1, further comprising the step of selecting a therapy for said subject based on said prevalence of perinucleolar compartments.

6. The method of claim 5, wherein said therapy comprises chemotherapy.

7. The method of claim 1, wherein said subject has been administered an anti-cancer therapy.

* * * * *